United States Patent [19]

Morrow

[11] Patent Number: 5,684,149
[45] Date of Patent: Nov. 4, 1997

[54] METAL COMPLEXES FOR PROMOTING CATALYTIC CLEAVAGE OF RNA BY TRANSESTERIFICATION

[75] Inventor: Janet R. Morrow, Williamsville, N.Y.

[73] Assignee: Research Foundation of State University of New York, Buffalo, N.Y.

[21] Appl. No.: 390,240

[22] Filed: Feb. 17, 1995

Related U.S. Application Data

[63] Continuation of Ser. No. 7,430, Jan. 22, 1993, abandoned.

[51] Int. Cl.$^6$ .......................... C07D 257/00; C07F 5/00; C12N 5/10; C07H 21/00
[52] U.S. Cl. .............................. 540/474; 540/465; 556/1; 556/6; 536/24.5; 536/23.1; 435/6; 435/325; 435/375; 435/377; 514/44; 514/79
[58] Field of Search .................. 514/44, 79; 536/23.1, 536/24.5; 435/240.2, 6, 325, 375, 377; 935/33, 34, 37, 38, 44; 424/DIG. 6; 540/474, 465; 556/1, 6

[56] References Cited

U.S. PATENT DOCUMENTS 5,049,667  9/1991  Schaefer et al. ..................... 540/474

FOREIGN PATENT DOCUMENTS

| | | | |
|---|---|---|---|
| WO 89/11868 | 12/1989 | WIPO | ............................ A61K 43/00 |
| 9008134 | 7/1990 | WIPO | ............................ C07C 309/14 |
| WO 91/13080 | 9/1991 | WIPO | ............................ C07H 17/00 |
| 9119730 | 12/1991 | WIPO | . |
| WO 91/19730 | 12/1991 | WIPO | ............................ C07H 23/00 |

OTHER PUBLICATIONS

S. Buøen et al., J. Chem. Soc., Chem. Commun. ('82) 1172–4.
B. Mahan, University Chemistry, 2nd Ed., Addison–Wesley, Reading MA ('69) p. 565.
J. Morrow et al. Inorg. Chem. ('93) 32:3357–61.
Mahan, Bruce, University Chemistry, 2nd Edition, Reading, MA, Addison–Wesley Publ. Co., Inc., 1969, p. 661.
Engelhardt et al., Australian J. of Chem., vol. 42 ('89) pp. 1045–1055.
Desreux, Inorg. Chem., vol. 19, (1980), pp. 1319–1324.
Dischino et al. J. of Lab. Compd.s & Radiopharmaceut. s, vol. 31 (1992) pp. 456–458.
Chow, C.S., et al. J. Am. Chem. Soc., vol. 112 (1990) pp. 2839–2841.
Ciesolka, J., et al. Eur. J. Biochem., vol. 182 (1989) pp. 445–450.
Stein, C.A., et al., Cancer Research, vol. 48, (1988) pp. 2659–2668.
Verspieren, P., et al. Gene, vol. 61 (1987) pp. 307–315.
Breslow, R., et al. P.N.A.S., vol. 88 (1991) pp. 4080–4083.
De Cola, L., et al. Inorg. Chem., vol. 25 (1986) pp. 1729–1732.
Chin et al., J. Am. Chem. Soc., 1989, vol. 11, pp. 4103–4105.
Butzow et al., Nature, 1975, vol. 254, pp. 358–359.
Breslow et al., Proc. Natl. Acad. Sci., 1989, vol. 86, pp. 1746–1750.
Menger et al., Ams. Chem. Soc., 1987, vol. 109, p. 3145.

Stein et al, Cancer Research, 1988, vol. 48, pp. 2659–2668.
Zuckermann et al., J. Am. Chem. Soc., 1988, vol. 110, pp. 1614–1615.
Zuckerman et al., J. Am. Chem. Soc., 1988, vol. 110, pp. 6592–6594.
Zuckerman et al., Proc. Natl. Acid. Sci. USA, 1989, vol. 86, pp. 1766–1770.
Corey et al., Biochemistry, 1989, vol. 28, pp. 8277–8286.
Barbier et al., J. Am. Chem. Soc., 1988, vol. 110, pp.6880–6882.
Breslow et al., J. Am. Chem. Soc., 1990, vol. 112, pp. 9621–9623.
Matsumoto et al., J. Chem. Soc., Chem. Commun., 1990, pp. 1050–1051.
Yoshinari et al., J. Am. Chem. Soc., 1991, vol. 113, pp. 5899–5359.
Stern et al., J. Am. Chem. Soc., 1990, vol. 112, pp. 5357–5359.
Modak et al., J. Am. Chem. Soc., 1991, vol. 113, pp. 283–291.
Shelton et al., Inorg. Chem., 1991, vol. 30, pp. 4295–4299.
Chu et al., Proc. Natl. Acad. Sci. U.S.A., 1985, vol. 82, pp. 963–967.
Le Doan et al., Biochemistry, 1986, vol. 25, pp. 6736–6739.
Uhlmann et al., Chem. Rev., 1990, vol. 90, pp. 544–584.
Oligodeoxynucleotides; Antisense Inhibitors of Gene Express, J.S. Cohen, ed. CRC press 1989.
Goodchild, Bioconjugate Chemistry, 1990, vol. 1, pp. 165–186.
Verspieren et al., An Acridine–linked Olig. Targeted to Common 5' End of Tryp. mRNAs Kills Cultured Para. Parasites, 1987, pp. 307–315.
Breslow et al., Effects of Metal Ions, 1991, PNAS vol. 88, pp. 4080–4083.
Ciesiolka et al., Probing the Environment of Lan. Binding Sites in Yeast tRNA by Specific Metal–Ion–Promoted Cleavages, EJB 1989, pp. 445–450.
Hay et al., A Lanthanum Macrocycle Catalysed Hydrolysis of a Phosphate Triester, JCSCC, 1990, pp. 714–715.
De Cola et al., Hexaaza Macrocyclic Complexes of Lanthanides, Inorg. Chem. 1986, pp. 1729–1732.
Chow et al., Shape–Selective Cleavage of tRNA by Transition–Metal Complexes, JACS 1990, pp. 2839–2841.

*Primary Examiner*—Charles C. P. Rories
*Attorney, Agent, or Firm*—Nixon, Hargrave, Devans & Doyle

[57] ABSTRACT

The present invention provides the first examples of metal complexes that show catalytic behavior in RNA transesterification under physiological relevant conditions i.e., 37° C. and neutral pH. The metal complexes are catalytically active and kinetically inert to metal ion dissociation.

The metal complexes are formed by the union of a central metal ion with a non-metallic ion or molecule. The metal ion comprises copper, zinc, cobalt, nickel, palladium, lead, iridium, maganese, iron, molybdenum, vanadium, titanium, ruthenium, bismuth, cadmium, yttrium, magnesium, rhodium, uranium, the transition metals and the Lanthanide metals. The non-metallic ion comprises a ligand or complexing agent. The preferred ligand is one which strongly chelates lanthanides, and more preferably, forms a cationic complex of the lanthanides.

14 Claims, 7 Drawing Sheets

Ln = La³⁺ or Eu³⁺

R = Me or H
Ln = La³⁺, Eu³⁺, Tb³⁺, Gd³⁺
for Ln = Eu
R = Me, Eu(L¹)³⁺

$X = CH_2 CH_2 OH, CH_6 CH_2 C(O)_1$
$= CH_2 C(O) NH_2$
$= CH_2 - OP(Me)(O)_2$
$= CH_2 C(O) NR_2$

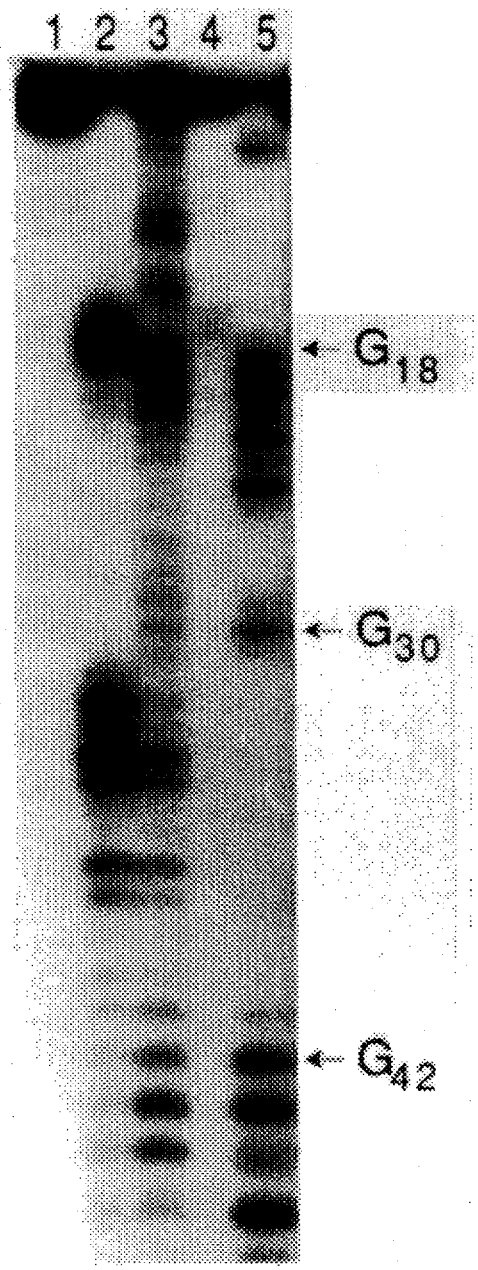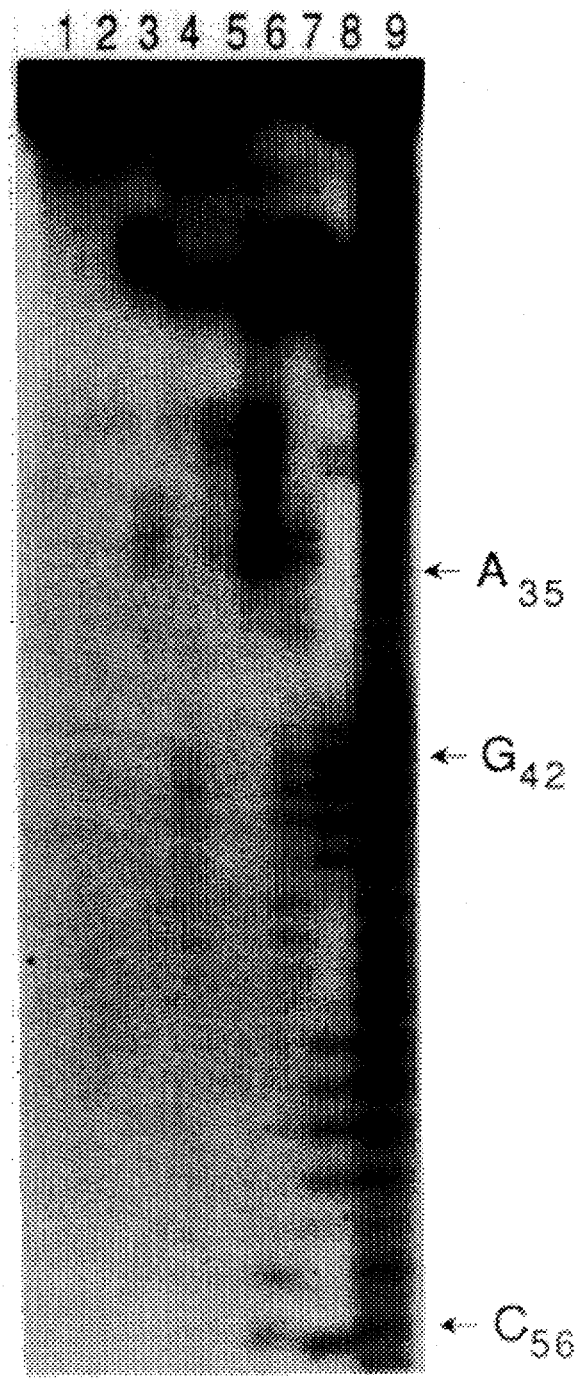
FIG.3(b)
FIG.3(d)

METAL COMPLEXES FOR PROMOTING CATALYTIC CLEAVAGE OF RNA BY TRANSESTERIFICATION

This application is a continuation of application Ser. No. 08/007,430, filed Jan. 22, 1993, now abandoned.

FIELD OF THE INVENTION

The present invention relates generally to RNA cleavage. More particularly, the invention relates to a method of catalytically cleaving oligomers of RNA by transesterification using novel macrocyclic complexes, and to attaching these complexes to antisense oligonucleotides for sequence-specific RNA cleavage.

BACKGROUND OF THE INVENTION

Recently hydrolysis of phosphate esters has received extensive investigation as reported in the art due to the relevance of this chemistry to biological systems, and specifically transition metal complexes have been examined as phosphate ester hydrolysis catalysts in order to model the reactions catalyzed by the ATPase and phosphatase classes of enzymes and also particularly as it relates to the manipulation of the phosphodiester backbone of ribonucleic acids (RNA). Such reported studies have generally employed activated p-nitrophenyl phosphate esters or phosphate anhydrides (ATP) as substrates (Cornelius, *Inorg. Chem.*, 1980, vol. 19, pp. 1286–1290; Norman et al., *J. Am. Chem. Soc.*, 1982, vol. 104, pp. 2356–2361). It has been reported that tetramine complexes of Co(III) are capable of promoting the hydrolysis of adenosine 3', 5'-monophosphate (cAMP) (Chin et al., *Can. J. Chem.*, 1987, vol. 65, pp. 1882–1884) and adenosine monophosphate (AMP) (Chin et al., *J. Am. Chem. Soc.*, 1989, vol. 11, pp. 4103–4105). Also, it is known that many divalent cations are capable of catalyzing the hydrolysis of RNA (Butzow et al., *Biochemistry*, 1971, vol. 10, pp. 2016–2027; and Butzow et al. *Nature*, 1975, vol. 254, pp. 358–359). Additionally, zinc ion in the presence of imidazole buffers has been shown to catalyze the hydrolysis of the RNA dimer 3', 5'-UpU at 80° C. (Breslow et al., *Proc. Natl. Acad. Sci.*, 1989, vol. 86, pp. 1746–1750).

The ribonuclease class of enzymes is known to hydrolyze RNA in vivo and in vitro (Blackburn et al., The Enzymes; Academic Press: New York, 1982; vol. 15, chapter 12, pp. 317–433), and the active site of many ribonucleases contains histidine residues believed to be involved in catalysis (Richards et al., Ibid., 1971, vol. 4, chapter 24, pp. 647–806). In order to model the reactions catalyzed by the ribonucleases, investigations into phosphate ester hydrolysis have been carried out using imidazole and imidazole derivatives as models for histidine. Such reported studies have generally employed activated p-nitrophenyl phosphate esters as the hydrolysis substrate, instead of RNA itself (Anslyn et al., *J. Am. Chem. Soc.*, 1989, vol. 11, pp. 5972–5973, and Anslyn et al., Ibid., pp. 8931–8932). These activated esters are more easily studied than the true biological substrates for two reasons: (1) they are more easily hydrolyzed, and (2) since the product p-nitrophenolate anion has a strong characteristic color, the reaction may be followed by simple spectrochemical techniques. While these analogues are convenient models for biological substrates, they are not accurate models (Menger et al., *Ams. Chem. Soc.*, 1987, vol. 109, p. 3145). Stein et al, *Cancer Research*, 1988, vol. 48, pp. 2659–2668, gives a detailed review on the application of antisense oligodeoxynucleotides as modulators of gene expression and concludes by proposing a more subtle and effective approach would be to attach a chemical group to the oligomer that can result in localized catalytic hydrolysis of RNA. This technique would be more specific than the use of a radical-producing group such as iron EDTA. Stein, et al, theorizes that a suitable RNA hydrolysis group would be an imidazole group, which is known to be involved in phosphodiester hydrolysis in the active site of ribonuclease enzymes.

PCT International Patent Application WO 88/04300 published on Jun. 16, 1988 discloses RNA enzymes or ribozymes, acting as endoribonucleases, as catalyzing the cleavage of RNA molecules with a sequence specificity of cleavage greater than that of known ribonucleases and approaching that of the DNA restriction endonucleases, thus serving as RNA sequence-specific endoribonucleases. However, ribozymes are entirely or partly comprised of RNA itself, and therefore are chemically and enzymatically highly unstable. Such instability detracts from the practical applicability of RNA hydrolysis agents. Also ribozymes presently are available only at a high cost due to limitations of very low production volumes through molecular biology techniques.

Chen et al., *J. Am. Chem. Soc.*, 1988, vol. 110, pp. 6570–6572, describes that 1,10-phenanthroline-copper(II) is effective for targeted cleavage of both RNA and DNA and thus is useful for sequence-specific cleavage of RNA. This teaching is directed to oxidative cleavage of RNA by metal complexes linked to DNA at a temperature of 65° C. as opposed to under physiologically relevant conditions. Further, the ancillary reagents, in the quantities required to drive the oxidative degradation of RNA, are not compatible with living cells and the 1,10-phenanthrolinecopper-oligodeoxynucleotide conjugate is itself degraded.

Schultz and coworkers in a series of articles (Corey et al., *J. Am. Chem. Soc.*, 1988, vol. 110, pp. 1614–1615; Zuckerman et al., *J. Am. Chem. Soc.*, 1988, vol. 110, pp. 6592–6594 and Zuckerman et al., *Proc. Natl. Acid. Sci. USA*, 1989, vol. 86, pp. 1766–1770) have described the preparation of site-selective DNA and RNA hydrolysis agents comprised of an enzyme (staphylococcal nuclease, ribonuclease S, or mutants of these parent enzymes) covalently linked to oligonucleotides. In one report (Corey et al., *Biochemistry*, 1989, vol. 28, pp. 8277–8286), the location of the linker arm and its length were varied, which resulted in changes in catalystic efficiency and site of cleavage. However, the nucleic acid cleavage behavior is provided by an enzyme and (1) enzymes are subject to proteolytic degradation by other enzymes; (2) staphylococcal nuclease is dependant on added calcium for its activity; (3) ribonuclease S is a noncovalent complex comprised of the S-protein and S-peptide derived from ribonuclease A, and this complex is subject to dissociation which results in loss of cleavage efficiency and specificity; (4) oligonucleotide-staphylococcal nuclease conjugates were found to cleave DNA as well as RNA thus lacking specificity for RNA hydrolysis alone. Furthermore, this high activity limits the specificity of the enzyme-based systems because nonspecific cleavage events are common, and the specificity of the enzymes were artificially increased by lowering the temperature below physiologically relevant values (i.e. to 0° C.).

Another approach, RNA cleavage by transesterification, is much more difficult to accomplish than is oxidative cleavage of nucleic acids (DNA or RNA). Reagents that cleave RNA by promoting transesterification of the phosphate diester linkage of RNA have been the subject of recent studies (Barbier et al., *J. Am. Chem. Soc.*, 1988, vol. 110, pp.6880–6882; Breslow et al., *Proc. Nat. Acad. Sci. U.S.A.*, 1989, vol. 86, pp.1746–1750; Breslow et al., *J. Am. Chem. Soc.*, 1990, vol 112, pp. 9621–9623; Matsumoto et al., *J. Chem. Soc., Chem. Commun.*, 1990, pp. 1050–1051; Yoshinari et al., *J. Am. Chem. Soc.*, 1991, vol. 113, pp. 5899–5359; Stern et al., *J. Am. Chem. Soc.*, 1990, vol. 112, pp. 5357–5359; Modak et al., *J. Am. Chem. Soc.*, 1991, vol. 113, pp. 283–291; and Shelton et al., Inorg. Chem., 1991, vol. 30, pp. 4295–4299). Cleavage of RNA by transesterification has many advantages over oxidative cleavage, including the possibility of religation of fragments, the high degree of selectivity for cleavage of RNA over DNA (Butzow et al., *Nature*, 1975, vol. 254, pp. 358–359), and the elimination of diffusible oxygen radicals that are often produced in metal-ion-promoted oxidative cleavage of nucleic acids. The latter two are important advantages because the use of metal complexes that promote oxidative cleavage of nucleic acids may result in destruction of the ligand (Chu et al., *Proc. Natl. Acad. Sci. U.S.A.*, 1985, vol. 82, pp. 963–967; and Le Doan et al., *Biochemistry*, 986, vol. 25, pp. 6736–6739).

PCT International Patent Application published under number WO 91/19730, published on Dec. 26, 1991, discloses hydrolytic cleavage of RNA at physiological relevant conditions using metal complexes which perform as synthetic analogs for enzymes or ribozymes in the hydrolysis of RNA. Also disclosed, is the sequence-directed hydrolyric cleavage of RNA by a metal complex covalently linked to a nucleoside, nucleotide or oligodeoxynucleotide. However, cleavage is performed with excess free metal complex. Thus, it is not possible to determine what actually cleaves the RNA. Furthermore, the Examples provided show cleavage occurring at multiple sites, not site-specific.

To date, however, while many organic and inorganic reagents as previously described cleave RNA it is only when present in large excess, and cleavage at 37° C. with catalytic amounts of compound has not been demonstrated.

One of the most significant applications of RNA transesterification catalysts is the possibility of forming potent antisense oligonucleotides by attachment of a catalytic cleaving group to the Oligo (Stein et al., *Cancer Res.*, 1988, vol. 48, pp. 2659–2688). An antisense oligonucleotide with an attached cleaving group able to participate in the catalytic destruction (several copies of mRNA per antisense oligonucleotide) of selected sequences of RNA could be effective in inhibition of gene expression.

The synthesis of various classes of antisense oligonucleotides and their use in selective suppression of gene expression has been studied by Stein et al., *Cancer Res.*, 1988, vol. 48, pp. 2659–2668; Uhlmann et al., *Chem. Rev.*, 1990, vol. 90, pp. 544–584; Oligodeoxynucleotides; Antisense Inhibitors of Gene Express, J. S. Cohen, ed. CRC press 1989; Goodchild, *Bioconjugate Chemistry*, 1990, vol. 1, pp. 165–186; Englisch et al., *Chem. Int. Ed. Engl.*, 1991, vol. 30, pp. 613–722. The use of crosslinking agents and cleaving agents has been discussed as a means of improving the potency of the antisense oligonucleotide. To date, however, there are no good cleaving agents that are rapid, specific and which could survive in vivo conditions.

SUMMARY OF THE INVENTION

The primary object of the present invention is to provide a method of catalytically cleaving RNA by transesterification using novel metal complexes.

Another object of the invention is to attach such complexes to oligonucleotides for sequence-specific RNA cleavage (inhibition of gene expression).

Accordingly, there is provided a method of catalytically cleaving oligomers of RNA by transesterification comprising providing a metal complex which is catalytically active and kinetically inert to metal ion dissociation under in vivo conditions and promoting the transesterification of RNA with the complex.

In one embodiment of the invention, the metal complex is a macrocyclic complex formed by the union of a central metal ion with a non-metallic ion or molecule. The metal ion can comprise copper, zinc, cobalt, nickel, palladium, lead, iridium, maganese, iron, molybdenum, vanadium, titanium, ruthenium, bismuth, cadnium, magnesium, rhodium, uranium, a transition metal, yttrium and the Lanthanide metals. The Lanthanide metals (elements 57–71) and yttrium (element 39) are preferred.

The non-metallic ion preferably comprises a ligand, chelate or complexing agent. For large metal ions such as the lanthanides(III), ligands that provide six or more donor atoms are preferred. The coordination chemistry of the lanthanides is distinct from the transition metals and Zn(II). Thus, ligands should be carefully constructed for the lanthanides(III) which can be different from those that work with the transition metal ions. Ligands for any of the metal ions within the scope of the invention need not form thermodynamically stable complexes with the metal ions. It is sufficient that they are kinetically inert to metal ion release. Accordingly, macrocyclic ligands can form kinetically inert complexes with labile metal ions if properly designed. Also, tetraazamacrocycle ligands strongly chelate the transition metal ions and Zn(II).

Preferably, the ligand is one which strongly chelates the Lanthanides, and forms a cationic complex. For example, classes of ligands which bind the Lanthanide metals and are inert to metal ion release include: (1) hexadentate Schiff-base ligands; (2) 2.2.1 cryptates; and (3) the cyclen derivatives with four pendent groups, and are represented by the following general formulas:

Class (1)

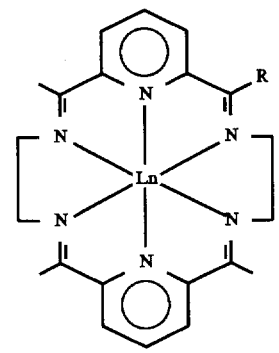

wherein

Ln=La$^{3+}$ or Eu$^{3+}$ or Tb$^{3+}$ or Gd3+ or, and

R=Me or H.

Class (2)

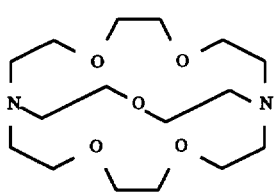

Class (3)

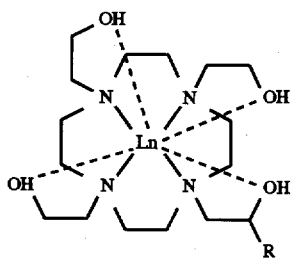

wherein

Ln=La3+ or, Eu$^{3+}$; and

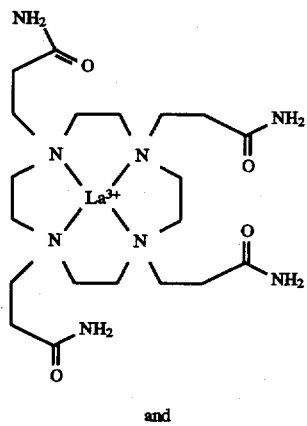

and

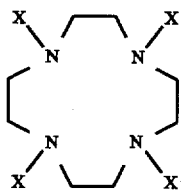

wherein x=$CH_2CH_2OH$ or $CH_2CH_2C(O)NH_2$ or $CH_2C(O)NH_2$ or $CH_2C(O)NR_2$ (R=alkyl) or $CH_2$—$O(Me)(O)_2$—. Also, cyclam, cyclen and derivatives thereof can be used.

In another embodiment of the invention, there is provided a method of inhibiting gene expression (m-RNA translation) under in vivo conditions comprising providing an oligonucleotide having attached thereto a catalytic metal complex effective for promoting catalytic cleavage of RNA and inhibiting m-RNA translation by formation of a DNA-RNA hybrid followed by cleavage of the RNA strand. The catalytic oligonucleotide-metal complexes of the invention are effective for sequence-specific RNA cleavage. The catalytic oligonucleotides of the invention are also useful in the suppression of RNA processing.

DETAILED DESCRIPTION OF THE INVENTION

Figure 1C:
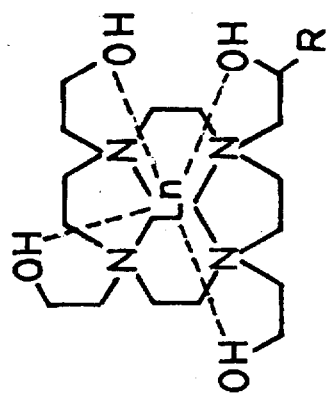
FIG. 1(a–e) shows the structures of classes of ligands of the present invention.

The present invention provides the first example of a macrocyclic complex that shows catalytic behavior in RNA transesterification. Complexes have been developed that catalyze RNA cleavage by transesterification under physiological relevant conditions. Some of the complexes are unique in that catalytic turnover is observed in RNA cleavage when excess RNA to complex is present. In addition, it was found that these complexes hydrolyze phosphate diesters such as 2',3'-cyclic adenosine monophosphate and that some have the unique ability to recognize certain features of transfer RNA and may be useful as a structural probe of RNA.

As used herein, "complex(es)" or "metal complex(es)" refer to the synthetic catalysts of the invention for promoting cleavage of oligomers of RNA by transesterification under physiological relevant conditions. "Physiological relevant conditions," as used herein, refer to cellular conditions present in vivo i.e., temperature range of about 32° C. to 37° C. The complexes of the invention are kinetically inert to metal ion dissociation under in vivo conditions and highly catalytically active.

The metal complexes (also referred to as coordination compound) of the invention are formed by the union of a metal ion with a nonmetallic ion or molecule, such as, a ligand or complexing agent. The metal ion of the complex can be any metal which is effective in catalyzing RNA. Typical metals include copper, zinc, cobalt, nickel, palladium, lead, iridium, maganese, iron, molybdenum, vanadium, titanium, ruthenium, bismuth, cadnium, yttrium, magnesium, rhodium, uranium, the transition metals and the Lanthanide metals. The Lanthanide metals and yttrium (elements 39 and 57–71,) are preferred. Preferably, the metal complexes are macrocyclic complexes.

"Ligand" as used herein, refers to a molecule, ion or atom that is attached to the central atom (metal) of the complex (coordination compound). Preferably, the ligand is a strong chelate of the metal ion, neutrally charged, and forms cationic complexes with the metal that are kinetically inert to metal ion release. Classes of Lanthanide(III) ligands within the scope of the invention include hexadentate Schiff-base ligands; 2.2.1 cryptates; cyclam derivatives and the cyclen derivatives with four pendent groups. Examples of cyclam derivatives include 2'pyridine and 4'pyridine. It can be advantageous in certain cases to use lanthanide(III) complexes of cyclen derivatives utilizing mixed pendent groups. Such examples includes a cyclen bearing an acetate and three hydroxyethyl groups or a cyclen bearing two acetates and two carbamoylmethyl groups. Advantages of these types of complexes include increased stability of the complex with more acetate groups and modifying the reactivity of the complex by the addition of various groups such as acetates. Synthesis of the lanthanide(III) complexes is similar to that for the lanthanide(III) DOTA complexes as described by Desreux, Inorg. Chem., 1980, vol. 19, p. 1319, which disclosure is hereby incorporated by reference. Because of the tremendous number of variations of the cyclen derivatives by changing pendent groups and using mixed pendent groups, this class of ligand is preferred for Lanthanides. For example, the ligand DOTA forms some of the strongest complexes known with Gd(III), La(III) and Eu(III). The overall formation constant for Gd(DOTA) is $10^{22}$ and the complex is kinetically inert to metal ion release. It is contemplated that the 12-membered macrocycle was a reasonable framework to begin with and addition of neutral pendent groups would complete the coordination sphere. The synthesis and solution properties of the lanthanum(III) and europium(III) complexes of 1,4,7,10-tetrakis(2-hydroxyethyl)-1,4,7,10-tetraazacyclododecane (THED) and a Eu(THED)$^{3+}$ are disclosed hereinafter. These complexes exhibited resistance to lanthanide (metal ion) release in water at 37° C.

Figure 1B:
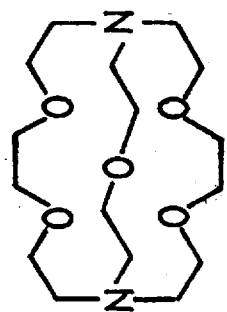
Figure 1A:
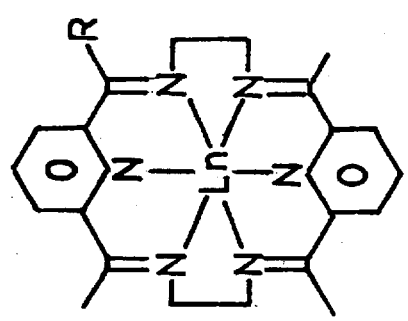

With reference to FIG. 1(a), the general formula for the hexadentate Schiff-base ligand of the invention is shown wherein Ln=La$^{3+}$ or Eu$^{3+}$ or Tb$^{3+}$, or Gd$^{3+}$, and R=Me or H.

Figure 1E:
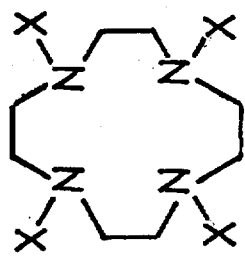
Figure 1D:
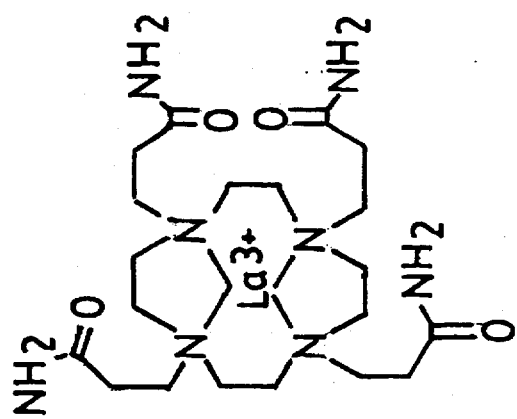

With reference to FIG. 1(b), the formula for Eu$^{(III)}$ complex of the 2.2.1 cryptate class is shown. With reference to FIGS. (c–e) variations of the cyclen derivatives with four pendent groups are shown. FIG. 1(c) shows THED wherein Ln=La$^{3+}$ or, Eu$^{3+}$. FIG. 1(d) shows TCC and FIG. 1(e) shows the general formula for the cyclen derivatives wherein x=CH$_2$CH$_2$OH or CH$_2$CH$_2$C (O) NH$_2$ or CH$_2$C (O) NH$_2$ or CH$_2$—OP(Me) (O)$_2$ or CH$_2$C (O)NR$_2$ (R=alkyl). It is understood that any monodentate, bidentate or polydendate ligand which can form a metal complex which is kinetically inert to metal ion dissociation under in vivo conditions and highly catalytically active can be used.

In another embodiment of the invention, the catalytic complexes are attached to oligonucleotides thereby forming potent catalytic oligonucleotides for sequence-specific RNA cleavage. As used herein, the term "oligonucleotide" includes oligodeoxynucleotides, antisense oligodeoxynucleotides and oligodeoxynucleotide analogs that are effective at molecular recognition by Watson-Crick or Hoogsteen basepairing. Preferably, the complexes of the invention are attached to antisense oligonucleotides. Examples of such oligodeoxynucleotide analogs include those with nonionic internucleotide linkages such as alkylphosphotriesters, alkylphosphonates and alkylphosphoramidates (as described by Miller, "Oligodeoxynucleotides Antisense Inhibitors of Gene Expression," J. S. Cohen, Ed. CRC Press, Florida, 1989, Chapter 4 and references therein, which disclosure is hereby incorporated by reference); compounds with sulfur-containing internucleotide linkages such as phosphorothioates and phosphorodithioates; Cancer Research, 1988, and alpha-oligodeoxynucleotides. Other oligodeoxynucleotides analogs which can be used include those with internucleotide linkages such as activated carbonyl, isothiocyanates and bromoacetimides. carbonate, acetate, carbamate, dialkyl and diarylsilyl groups and methyeneoxy(methylimino) groups.

Several metal complexes have been shown to promote the transesterification of simple oligomers of RNA at 37° C. as described by Stein, et al. and Modak et al., (cited elsewhere herein). However, in order for a metal complex attached to an oligonucleotide to function in vivo, the complex must be inert to release of the metal ion if the synthetic nucleases is to arrive intact to interact with mRNA. Accordingly, the present invention provides metal complexes that promote transesterification of RNA at 37° C. and that are inert with respect to metal release. The Lanthanide complexes of the invention are preferred because lanthanide(III) salts are effective in promoting phosphate ester hydrolysis as described by Butcher et al., J. Am. Chem. Soc., 1955, Vol. 77, pp. 2420–2424; and Hay et al., J. Chem. Soc. Common., 1990, pp. 714–715, which disclosures are hereby incorporated by references, and transesterification of RNA as described by Eichhorn et al., J. Biopolymers, 1965, Vol. 3, pp. 74–94; Baumann et al., Biochem., 1954, Vol. 328, pp. 86–96; and Riordorf et al., Biopolymers, 1976, pp. 1491–1504, which disclosures are hereby incorporated by references. The hexadentate ligand L$^1$ forms complexes with all lanthanide(III) ions as described by DeCola et al., Inorg. Chem., 1986, Vol. 25, pp. 1729–1732, which disclosure is hereby incorporated by reference. Five of these complexes were studied for their resistance to decomposition under a variety of conditions. Percent decomposition was determined by the use of $^1$H NMR for Eu (L$^1$)$^{3+}$, La(L$^1$)$^{3+}$ and Lu(L$^1$)$^{3+}$ or by the use of UV-vis spectroscopy for Tb (L$^1$)$^{3+}$ and Gd (L$^1$)$^{3+}$. After 3 days at 37° C. and pH 7.0, Lu(L$^1$)$^{3+}$ had completely decomposed, Gd (L$^1$)$^{3+}$ and Tb (L$^1$)$^{3+}$ had undergone a moderate degree of decomposition (26% and 36%, respectively), and La (L$^1$)$^{3+}$ and Eu(L$^1$)$^{3+}$ had undergone little decomposition (8% and less than 5%, respectively). Experiments performed under more rigorous conditions (see Table I) suggested that Eu(L$^1$)$^{3+}$ was overall the most inert to metal loss.

Extensive cleavage of the dinucleotide adenylyl-3', 5'-uridine3'-monophosphate (ApUp) or of oligomers of adenylic acid (A$_{12}$–A$_{18}$) was promoted at 37° C. after 4 hours by several lanthanide complexes (See Table I). Precautions were taken against contaminations by ribonucleases, including the sterilization of all equipment and solutions. Reactions with metal complex run in the presence of excess EDTA showed no RNA cleavage. In the absence of Ln(L$^1$)$^{3+}$, no cleavage of ApUp was observed over a three day period, and less than 2% cleavage of A$_{12}$–A$_{18}$ was observed after four hours. This was significant in view of the fact that other hexadentate ligands such as EDTA form lanthanide(III) complexes that are completely inactive in RNA cleavage under similar conditions.

TABLE I

RNA Cleavage by Lanthanide (III)
Complexes and Their Decomposition in Water at 37° C.

| complex[a] | ph 2.5[b] (%) | DTPA[c] (%) | ApUp cleavage[d] (%) | A$_{12}$–A$_{18}$ cleavage[e] (%) |
|---|---|---|---|---|
| La (L$^1$)$^{3+}$ | 0.0 | 100 | 20 | 70 |
| Eu (L$^1$)$^{3+}$ | 8.0 | 20 | 41 | 89 |
| Gd (L$^1$)$^{3+}$ | 18 | 36 | 27 | 93 |
| Tb (L$^1$)$^{3+}$ | 23 | 63 | 57 | 81 |
| Lu (L$^1$)$^{3+}$ | 100 | 100 | | |

[a]Nitrate, or mixed acetate chloride salts; refs 16 and 17.
[b]Percent decomposition after 20.5 h, 0.01 M Ln (L$^1$)$^{3+}$.
[c]pH 7.0, percent decomposition after 20.5 h, 0.01 M Ln (L$^1$)$^{3+}$, 0.02 M DTPA (DTPA = diethylenetriaminepentaacetic acid).
[d]Percent cleavage after 4.0 h, 490 µM Ln (L$^1$)$^{3+}$, 20 µM ApUp, pH = 7.15, 0.01 M HEPES buffer, 0.1 M NaNo$_3$. In the absence of Ln (L$^1$)$^{3+}$, no cleavage was observed.
[e]Percent cleavage after 4.0 h, 200 µM Ln (L$^1$)$^{3+}$, 190 zM A$_{12}$–A$_{18}$ (adenosine concentration), pH = 7.00, 0.01 M HEPES buffer. In the absence of Ln (L$^1$)$^{3+}$, observed cleavage was less than 2%.

It is believed that an overall positive charge on the lanthanide complex may be necessary for the complex to be active. For further information, see Morrow et al., Abstracts of Papers; 4th Chemical Conference of North America, N.Y., August 1991; and *American Chemical Society;* Washington D.C., 1991; INORG 406, which disclosures are hereby incorporated by reference. Pseudo-first-order rate constants for cleavage of ApUp by 490 μM $Eu(L^1)^{3+}$ or of $A_{12}$–$A_{18}$ by 160 μM $Eu(L^1)^{3+}$ are 0.14 $h^{-1}$ and 15 $h^{-1}$, respectively. This rate data establishes that $Eu(L^1)^{3+}$ is one of the most efficient metal complexes to promote transesterification of RNA oligomers at 37° C. and neutral pH. Lanthanide(III), zinc(II), and lead(II) complexes are less efficient in promoting ApUp cleavage, as are several copper(II), nickel)II), and zinc(II) complexes in promoting the cleavage of $A_{12}$–$A_{18}$ under similar conditions.

Figure 2:
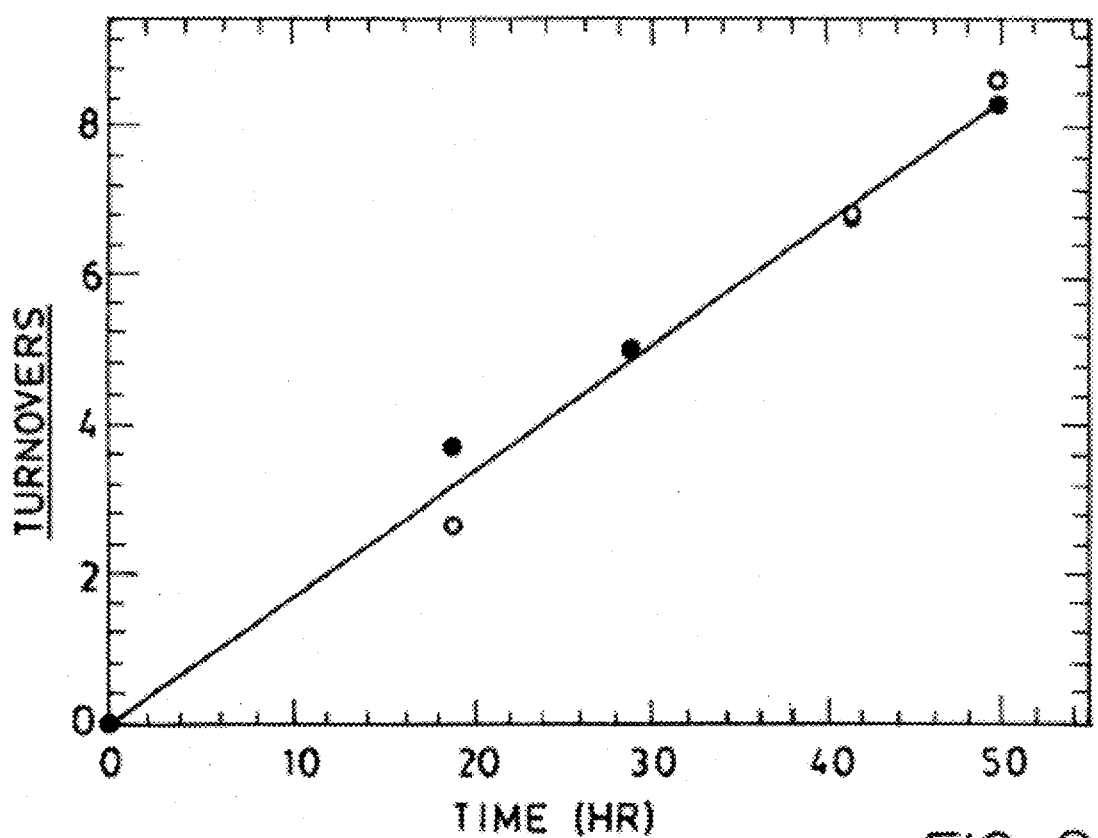
FIG. 2 shows a plot of catalytic turnovers versus time for the cleavage of ApUp by Eu(L$^1$)$^{3+}$.

Catalytic turnover was studied with ApUp as substrate because the products are easily identified according to the procedure of Shelton et al., cited elsewhere herein, which disclosures is hereby incorporated by reference. With catalytic amounts of $Eu(L^1)^{3+}$ (120 μM), the major products were initially adenosine cyclic 2', 3'-monophosphate (2', 3'-cAMP) and uridine 3'-monophosphate. Small amounts of the hydrolysis product adenosine 3'-monophosphate (3'-AMP) were observed after several turnovers. at 10-fold or greater excess of ApUp to $Eu(L^1)^{3+}$, a further increase in dinucleotide concentration resulted in no further increase in the rate of transesterification. With reference to FIG. 2, there is shown a plot of catalytic turnovers versus time for the disappearance of dinucleotide or appearance of products 2'3'-cAMP and 3'-AMP. The straight line that is observed for several turnovers suggests that $Eu(L^1)^{3+}$ shows good catalytic behavior. Initial [ApUp]=$2.66\times10^{-3}$M; [$Eu(L^1)^{3+}$]= $1.20\times10^{-4}$M. $3.0\times10^{-2}$M HEPES buffer, pH 7.10, 37° C. "O" is based on [ApUp]. "●" is based on SUM of [2',3'-cAMP] and [3'-AMP] products.

Another important aspect in the synthesis of the lanthanide complexes of the invention is the size of the macrocycle ring. For example DOTA complexes (12-membered ring) are much more stable than are TETA complexes (14-membered ring). Attempts to synthesize lanthanum(III) complexes of THEC (1,4,8,11-tetrakis(2-hydroxyethyl)1,4, 8,11-tetrazacyclotetradecane) failed to produce complexes that were inert in water. The 12-membered macrocycle is highly sterically efficient for coordination of the early to middle lanthanides. Thus use of the cyclen (12-membered ring) framework appears to be necessary to the design of kinetically inert complexes especially if weak ligating groups such as hydroxy ethyl are utilized.

Variation of the ionic radius of the lanthanide may be used to form more inert complexes. The inertness of a macrocyclic complex to metal ion release is highly dependent on the size of the lanthanide ion. Neutral and negatively charged complexes of the lanthanides are much less active in RNA cleavage than are the complexes. La(EDTA) does not promote cleavage of ApUp at 37° C., pH=8.

A positively charged complex binds better to the negatively charged backbone of phosphate diesters of RNA. Other factors such as Lewis acidity of the metal complex are undoubtably influenced by the overall charge on the complex and the type of ligating groups. For example polyaminocarboxylate ligands that give complexes with a neutral or negative charge such as DOTA do not bind hydroxide (Bryden et al., *Anal. Chem.,* 1981, vol. 53, p. 1418, which disclosure is hereby incorporated by reference.

The following Examples illustrate the synthesis and dynamic properties of kinetically inert lanthanum(III) and europium(III) complexes of 1,4,7,10 tetrakis(2-hydroxyethyl)1,4,7,10-tetraazacyclododecane and 1,4,7,10-tetrakis(2-carbamoylethyl)-1,4,7,10-tetraazacyclododecane to further illustrate the present invention. These Examples are not to be taken as limitations on the scope of the invention.

EXAMPLE I

METHODS

1. Experimental

The free base form of cyclen (1,4,7,10-tetraazacyclododecane) was generated by passing the tetrahydrochloride salt (Parish Chemicals or Strem Chemicals) through a Dowex 1X8-200 anion exchange column (30 cm×2.5 cm, hydroxide form). $La(SO^3CF^3)^3$ with $Eu(SO^3CF^3)^3$ were obtained by treating the respective lanthanide oxides with concentrated trifluoromethanesulfonic acid. 1,4,7,10-tetrakis(2-hydroxyethyl)1,4,7,10-tetraazacyclododecane (THED) was prepared by treating cyclen with a 50% excess of ethylene oxide in either absolute ethanol or water at 0° for 3 to 4 hours. The ligand was recrystallized from isopropanol and isolated in 50% yield. 1,4,7,10-tetrakis(2-carbamoylethyl)-1,4,7,10-tetraazacyclododecane (TCC) was prepared by treating cyclen (0.2 g, 1.16 mmol) with acrylamide (0.33 g, 4,64 mmol) in 6 mL of methanol. The mixture was refluxed for 48 hours. The methanol was removed in vacuo to give a sticky white solid that could be recrystallized from methanol (90% yield). All chemicals used were of analytical grade. Acetonitrile was dried over $CaH_2$. Milli-Q purified water was used for kinetic experiments.

THPD (1,4,7,10-tetrakis(2-hydroxypropyl)-1,4,7,10-tetraazacyclododecane) was prepared by treating cyclen with propylene oxide as described by Hancock et al., *Inorg. Chem. Acta,* 1988, pp. 229–238, which disclosure is hereby incorporated by reference.

TCMC (1,4,7,10-tetrakis(carbamoylmethyl)-1,4,7,10-tetraazacyclododecane) was prepared by treating cyclen with a five-fold excess of 2-chloroacetamide in methanol in the presence of triethylamine (five-fold excess) followed by recrystallization of the ligand from methanol.

2. La (THED) $(SO_3CF_3)_3$

The lanthanum complex of THED was prepared in acetonitrile by the following method. $5.75\times10^{-4}$ mol was refluxed under nitrogen in a mixture of 50 mL of dry acetonitrile and 5.6 mL of trimethylorthoformate for several hours. THED ($5.75\times10^{-4}$M) dissolved in acetonitrile was introduced by cannula into the solution containing lanthanum. The mixture was reflexed for an hour. The acetonitrile solution was concentrated in vacuo and methylene chloride was added. The crystalline product was obtained in 60% yield. (Anal. calcd. for $C_{19}H_{38}N_4O_{14}F_9S_3La$: Cf 24.00; H 3.99; N, 5.88; La, 14.59. Found C, 24.20; H, 4.02; N, 5.74; La, 14,45. FABMS m/z 785 (la(THED)-$SO_3CF_3$), 635).

3. Eu (THED) $(SO_3CF_3)_3$

The europium complex of THED was prepared in a procedure similar to that for the lanthanum complex. A white power was isolated in 60% yield. (Anal. calcd. for $C_{19}H_{36}N_4O_{13}F_9S_3Eu$: C, 24.10; H, 3.80; N, 5.91; Eu, 16.05. Found Cr 23.82, H 3.82; Nr 5.69; Eur 16.29).

4. La (TCC) $(SO_3Cf_3)$ $La(SO_3CF_3)_3$ (0.323 g, 0.55 mmol) was refluxed under nitrogen in a mixture of dry acetonitrile (65 mL) and trimethylorthoformate (6.5 mL) for one hour. TCC (0.250 g) in a minimum amount of methanol was added and the reaction mixture refluxed for 3.5 hours. The acetonitrile was reduced in vacuo and a few drops of methylene chloride were added. White crystals were isolated in 50% yield. FABMS m/z 893 {(La (TCC) $(SO_3CF_3)_2)^+$}.

5. La(THPD)$(SO_3CF_3)_3$ and Eu(THPD)$(So_3Cf_3)_3$

These compounds were synthesized using a method similar to that for La(THED)$(SO_3CF_3)_3$. Crystallazation was induced from acetonitrile diethyl ether solutions.

6. LaTCMC $(SO_3CF_3)_3$

This compound was synthesized using a method similar to that for LaTCC$(SO_3CF_3)_3$. Analytical data was satisfactory.

7. $^1$H NMR and $^{13}$C NMR $^1$H NMR and $^{13}$C NMR spectra of La(THED)$^{13+}$ and Eu (THED)$^{3+}$, La (THPD)$^{3+}$, Eu (THPD)$^{3+}$, and La (TAC)$^{3+}$ were as expected for macrocycles coordinated through eight donor atoms of the cyclen ring and four pendent groups. Similar to the analogous DOTA complexes as described by Aime et al., Inorg. Chem., 1992, Vol. 31, pp. 4299, which disclosure is hereby incorporated by reference. A dynamic process was observed for all five complexes on the NMR time scale. At low temperatures (–40° C.) $^1$H NMR resonances could be assigned to eight different types of protons for the lanthanum complex or for the europium complex of THED. At 0° C. $^1$H NMR resonances could be assigned to ten different types of protons for La(TCC)$^{3+}$. This data is consistent with a solution structure similar to DOTA for the two lanthanum complexes and the europium complex. A single-crystal x-ray diffraction study of the La(TCC)$^{3+}$ complex had the lanthanum coordinated to four nitrogens of the cyclen ring and four oxygens of the amide groups.

EXAMPLE II

Metal Ion Release

At neutral or slightly basic pH, La(THED)$^{3+}$, La(THPD)$^{3+}$, Eu(THPD)$^{3+}$ and Eu(THED)$^{3+}$ were resistant to decomposition. Eu(THED)$^{3+}$ and Eu(THDD)$^{3+}$ are highly kinetically inert as monitored by NMR. Because the lanthanide complexes of the invention have potential therapeutic uses it was desirable to develop a more sensitive assay than NMR to detect decomposition of these complexes. Thus, an UV-vis assay to monitor decomposition was developed. At pH 6–7 it is possible to monitor the amount of decomposition by determining the concentration of free THED or THPD through its complexation to Cu$^{2+}$. The kinetics of decomposition can be monitored by following the production of Cu(THED)$^{2+}$ or Cu(THPD)$^{2+}$ over time since the complexation of Cu$^{2+}$ with THED is rapid relative to the rate of decomposition of the lanthanide complexes. For the lanthanum complex the reaction was first order in La(THED)$^{3+}$ and showed no dependence on the concentration of copper. A simple kinetic scheme consistent with these results has the La$^{3+}$ dissociating from the macrocycle with Cu$^+$ trapping the free macrocycle. For the Eu complexes in the presence of excess Cu$^{2+}$ no decomposition was observed after three days at room temperature. A few percent decomposition was observed at 37° C. after 20 hours, pH 6.85. The greater kinetic stability of Eu$^{3+}$ complex may be related to the better fit of the smaller Eu$^{3+}$ to the macrocycle.

The rate of decomposition of the lanthanum(III) complex of THED in the presence of Cu$^{3+}$ was monitored by following the increase in absorbance of a peak at 312 nm. Beer's law plots with varying concentrations of Cu(THED) (0.200 mM to 1.00 mM) gave an extinction coefficient of 6833 for the peak at 312 nm. Because of the slow rate of decomposition, most pseudo-first order rate constants were obtained by the method of initial rates. However, long runs typically showed good pseudo-first-order kinetics for over 4 half-lives. A reaction order of 1.00+/0.05 was obtained from experiments where the concentration of La(THED)$^{3+}$ was varied from 0.05 mM to 0.2 mM. The reaction solution was buffered at pH 6.00 by excess Cu(Cl)$_2$ and reaction solutions were tested at the end of kinetic runs to insure that pH had remained constant.

La(THED)$^{3+}$ was stable in aqueous solution, pH 7.5, room temperature for a few hours. Resonances attributed to free ligand was observed after approximately 6 hours at eighter pH 6.6 or 7.5. After 2 hours at room temperature, traces of free ligand was observed in solutions containing DTPA and La(THED). 24 hours after the addition of DTPA, most of the lanthanum was bound to DTPA and only a trace of complex remained. Eu(THED)$^{3+}$ and Eu(THPD)$^{3+}$ were more stable than either of the lanthanide complexes. No trace of free ligand was observed at pH 6.9, 37° C. after several hours. A similar study was conducted to determine if the decomposition of the europium complex (1 mM) was accelerated in the presence of t-RNA$^{phe}$ (2×10$^{-5}$M) at pH 7.5, 37° C. t-RNA$^{phe}$ binds Eu$^{3+}$. No free ligand was detected after five hours of incubation of the mixture.

EXAMPLE III

Tetraazamacrocycles of Cu(II), Zn(II), Cd(II) and Pb(II)

For an artificial nuclease to cleave RNA under in vivo conditions, it must be stable under in vivo conditions. For metal complexes this necessitates that the complex be either kinetically inert to metal ion release (large activation barrier to metal ion release) and/or thermodynamically extremely stable (large formation constant for metal and ligand). The Lanthanide complexes described in Example 1 are in the first category (kinetically inert). The complexes described in this Example are both inert to metal ion release and have a high formation constant.

Complexes of cyclam (1,4,8,11-tetraazacyclotetradecane) and cyclen (1,4,7,10-tetraazacyclosdodecane) were synthesized. Cyclam complexes of Zn(II), Cd(II) and cyclen complex of Cu(II) and Zn(II) cleave t-RNA$^{phe}$ after several hours, as shown in FIGS. 3(a-c). Formation constants for these complexes are high: log K (25° C.)=15.5, 11.7, 11.3, 24.8, 16.2, 15.9 respectively. The stability of these complexes and their ability to cleave RNA suggests they can be used as artificial nucleases.

Figure 3A:
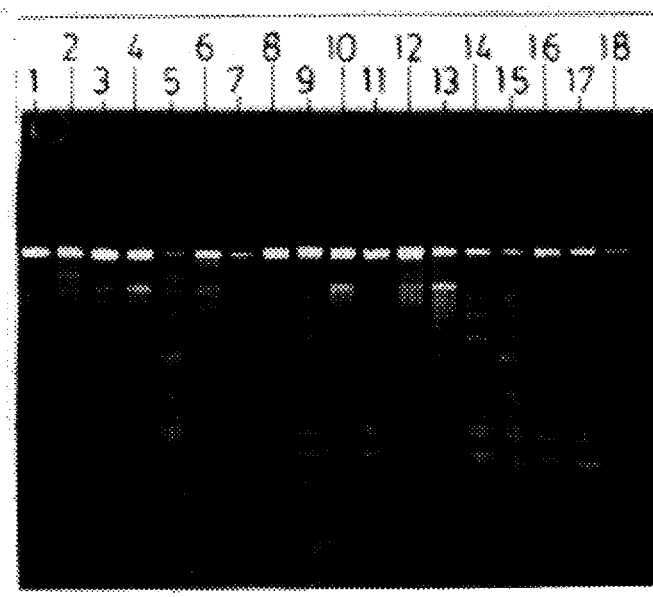
FIGS. 3 (a–d) are photographs of gels showing cleavage of t-RNA by cyclam and cyclen complexes.
Figure 3D:
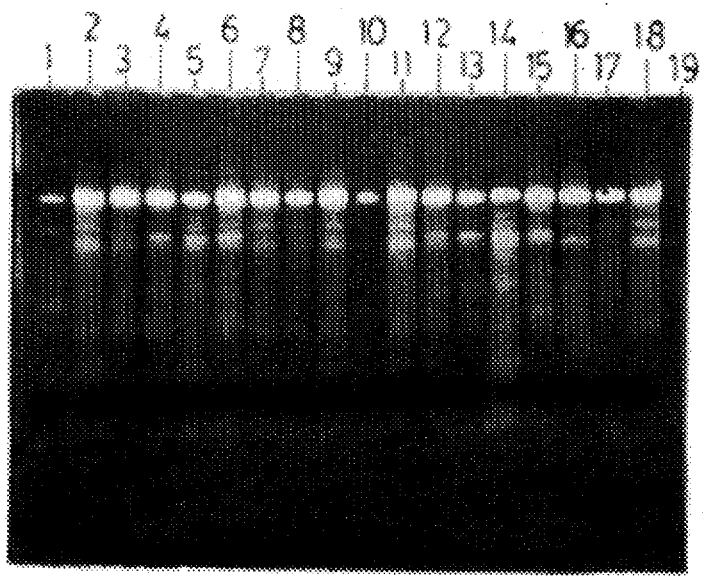

With reference to FIG. 3(a), (conditions of 1 mM complex, pH=7.5, 37 C, 2M Hepes buffer, t-RNA$^{phe}$=2.5× 10$^{-5}$M, 24 hour incubation) there is shown at Lane 1: control (no metal ion), Lane 2: CuCl$_2$, Lane 3: Ni (NO$_3$)$_2$, Lane 4: CoCl$_2$, Lane 5: Zn(NO$_3$)$_2$, Lane 6: Cd(NO$_3$)$_2$, lane 7: Cu(cyclam)$^{2+}$, Lane 8: Ni(cyclam)$^{2+}$, Lane 9: Co (cyclam)$^{3+}$, Lane 10: Zn (cyclam)$^{2+}$, Lane 11: Cd(cyclam)$^{2+}$, Lane 12: Zn(2'pyridine)$^{2+}$, Lane 13: Zn(4'pyridine)$^{2+}$, Lane 14: Cd(2'-pyridine), Lane 15; Cd(4'-pyridine), Lane 16: cyclam ligand alone, Lane 17: 2'-pyridine ligand alone, Lane 18: 4-pyridine ligand alone.

With reference to FIG. 3(b), there is shown cleavage of t-RNA$^{phe}$ by Eu (CH$_3$Co$_2$)$_3$, Zn(NO$_3$)$_2$ and Eu (L$^1$)$^{3+}$ (L$^1$ is 2,7,13,18-tetramethyl-3,6,14,17,23,24-hexaazatricyclo-(17.3.1.1) tetracosa-1(23), 2, 6, 8, 10,12 (24), 13,17,19,21-decane). Autoradiograms are of 8M urea denaturing polyacrylamide sequencing gels of t-RNA$^{phe}$ labeled with $^{32}$p at the 3'end. Approximately 1×10$^5$ cpm (B) or 5×10$^4$ cpm (A) of labeled t-RNA$^{phe}$ was loaded on the gel for each sample. Cold t-RNA$^{phe}$ was added to give a total concentration of t-RNA of 20 uM (1.3 mM nucleotide). Metal complex concentrations were 1 mM and hepes buffer was 0.4M. Reaction were run at pH 7.86, 37° C. for the times indicated. Nucleotides are counted from the 5'-end and labels denote the nucleotide which has cleaved (i.e., "$G_{18}$" signifies that the phosphate ester 3' to $G_{18}$ has been cleaved). A: Lane 1: control, Lane 2: $Eu(CH_3CO_2)_3$, 5 hours, Lane 3: $Eu(L1)^{3+}$, 5 hours, Lane 4: $Zn(NO_3)_2$, 5 hours, Lane 5: RNase $T_1$ (G specific, weak cleavage at sites other than G is sometimes observed), Lane 9: alkaline hydrolysis. B: Lane 1: control, Lane 2: control with oligonucleotide (20 uM, 400 uM phosphate), Lane 3: Eu $(CH_3CO_2)_3$, 10 min , Lane 4: Eu $(L^1)^{3+}$, 10 min., Lane 5: Eu $(L^1)^{3+}$ and 20 uM oligonucleotide, 10 min., Lane 6: Eu $(L^1)^{3+}$, 5 hours Lane 7: Eu $(L^1)^{3+}$ and 20 uM oligonucleotide, 5 hours, Lane 8: RNase $T_1$.

With reference to FIG. 3(c), it was determined whether cyclen complexes of Ni(II), Cu(II), Zn(II) and Co(III) cleave t-RNA under conditions of pH=7.5, 37° C., 2M Hepes, 1 mM complex, $2.5 \times 10^{-5}$ M t-RNA$^{phe}$. Lanes 1–9 are for incubation at 8 hours. Lanes 10–18 are for incubation for 24 hours. Lane 1: control (no metal ion), Lane 2: $CuCl_2$, Lane 3: Ni $(NO_3)_2$, Lane 4: $COCl_2$, Lane 5: Zn $(NO_3)_2$, Lane 6: Cu (cyclen)$^{2+}$, Lane 7: Ni (cyclen)$^{2+}$, Lane 8: Co (cyclen)$^{3+}$, Lane 9: Zn (cyclen)$^{2+}$. Lanes 10–18 are the same as above except for incubation for 24 hours.

EXAMPLE IV

RNA Cleavage and the Effect of RNA Structure

Figure 4A:
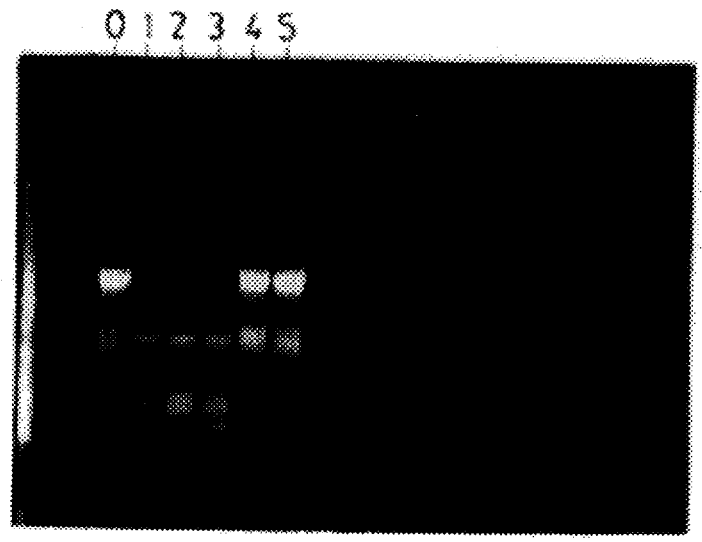
FIGS. 4 (a–b) are photographs of gels showing cleavage of radio labeled t-RNA by Eu(L$^1$)$^{3+}$ with and without DNA-RNA hybrid.

Experiments in the artificial nuclease field have been conducted with short, flexible single-stranded RNA strands as substrates. For example, dinucleotides or oligomers of adenylic acid ($Al_{12}$ to $Al_{18}$) have been used. The effect of RNA structure by studying cleavage of t-RNA has been examined along with cleavage of a DNA-RNA hybrid. With reference to FIG. 4, Eu(THED)$^{3+}$ and Eu (2.2.1 cryptate)$^{3+}$ cleave t-RNA rapidly. With reference to FIG. 4(a), cleavage of t-RNA$^{phe}$ by Eu(THED)$^{3+}$ under conditions of pH=7.5, 37° C., 2M Hepes, 1 mM complex, $2.5 \times 10^{-5}$M t-RNA$^{phe}$ is shown. Lane 1: control, Lane 2: Eu (Cl)$_3$, Lane 3: La (Cl)$_3$, Lane 4: Eu(THED)$^{3+}$, Lanes 5 and 6 other lanthanide complexes.

Figure 4B:
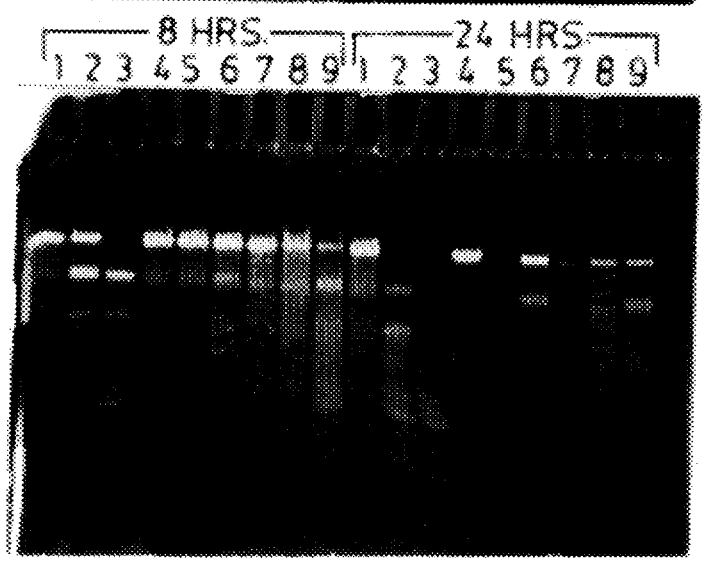

With reference to FIG. 4(b), cleavage of t-RNA$^{phe}$ by Eu (2.2.1 cryptate)$^{3+}$ under conditions of pH=7.5, 2M Hepes, 1 mM complex, $2.5 \times 10^{-5}$M t-RNA$^{phe}$ is shown. Lane 1: control, Lane 2: La (Cl)$_3$, Lane 3: Eu (2.2.1. cryptate)$_3$, Lane 4–8: cyclen complexes of Co (III), Ni(II), Cu(II), Zn(II), Lane 9: $EuCl_3$.

EXAMPLE V

Structure Specific Cleavage by Artificial Ribonucleases: Construction of Antisense Oligonucleotides Currently there is much interest in the design of artificial ribonucleases that cleave RNA by promoting transesterification at phosphate ester linkages. RNA transesterification catalysts have the potential of being much milder and more selective for RNA than are reagents which effect oxidative cleavage of RNA. A major impetus for the study of transesterification catalysts lies in the development of new antisense oligonucleotides that inhibit m-RNA translation by formation of a DNA-RNA hybrid followed by cleavage of the RNA strand. However, it is not apparent whether transesterification catalysts that readily cleave single-stranded RNA can effect cleavage of RNA in DNA-RNA hybrids or RNA with a large degree of secondary and tertiary structure. This information would be helpful in determining the best place to tether a transesterification catalyst to an antisense oligonucleotides. Unlike cleaving agents that produce diffusible radicals, a transesterification catalyst must be carefully positioned to interact with phosphate ester and/or ribose hydroxyl group. It has been demonstrated by applicant that RNA structure has a dramatic effect on the rate of cleavage by artificial ribonucleases based on metal complexes. The hexadentate Schiff base macrocyclic Eu(III) complex ((Eu(L$^1$)$^{3+}$), the most efficient metal RNA transesterification catalyst reported to date for single-stranded RNA, is unable to cleave RNA in a DNA-RNA hybrid. It is speculated that it is the conformation of RNA in a double-helical form which protects it from cleavage by metal transesterification catalysts.

Cleavage of t-RNA$^{phe}$ by (EuL$^1$)$^{3+}$ occurs at sites that are quite distinct from those observed for metal salts that insert into binding pockets of t-RNA$^{phe}$ (FIG. 4). Eu(L$^1$)$^{3+}$ promotes cleavage at $G_{18}$, $G_{19}$ and $G_{20}$ in the D-loop, $A_{44}$ and $G_{45}$ in the V loop plus $G_{42}$ and $G_{43}$ at the base of the double stranded anticorlon arm and $Al_{10}$ and $U_9$ in a short single-stranded section of RNA. La(L$^1$)$^{3+}$ gives an identical pattern (data not shown). A pH of 7.5 is optimal and the cleavage pattern is not changed by the presence of 1 mM Mg$^{2+}$ or 1M NaCl. Addition of 8M urea to t-RNA$^{phe}$ followed by incubation at 90° C. for one minute and rapid cooling prior to initiation of the cleavage reaction leads to the appearance of additional strong cleavage sites in the anticodon arm of t-RNA$^{phe}$. A 20-base oligodeoxynucleotide annealed to the t-RNA followed by incubation with Eu(L$^1$)$^{3+}$ led to the protection of all sites on the RNA sequence complementary to the DNA hybrid. Consistent with the formation of a new DNA-RNA hybrid, new exposed sites in the anticodon arm are cleaved in the presence of oligodeoxynucleotide. Long incubation times led to cleavage at almost every nucleotide with the exception of those predicted to be protected by the oligonucleotide.

The overall structure of t-RNA$^{phe}$ appears to be the most important factor in the sites cleaved by Eu(L$^1$)$^{3+}$ and, in contrast to early reports of base specific cleave of RNA by metal salts, there appears to be relatively little discrimination according to base sequence alone. The solution structure of t-RNA$^{phe}$ (FIG. 3) has been probed by compounds that exhibit shape-selective cleavage or cleave only at solvent accessible nucleotides (Chow et al., *J. Am. Chem. Soc.*, 1990, VOL. 112, PP. 2839–2841; Chow et al., *Biochemistry*, 1992, vol. 31, pp. 972–978; and Peattie et al., *Proc. Nat. Acad. Sci. USA*, 1980, vol. 77, pp. 4679–4682, which disclosures are hereby incorporated by reference. All cleavage sites with Eu(L$^1$)$^{3+}$ map onto a three dimensional structure representation in the central hinge section of the t-RNA "L" shape. With the exception of $G_{42}$ and $G_{43}$ which are at the end of a short helical section, these sites are in single-stranded regions. It is difficult to predict how binding of the europium complex modifies the intricately balanced structure of t-RNA and studies are underway to determine whether metal complexes cleave RNA in long sections of double-stranded RNA. No cleavage is observed in the single-stranded anticodon loop. At this timer applicant has not yet been determined whether this is because of binding differences or reactivity differences. However, applicant has found that nucleotides in the D-loop are more readily cleaved by many metal complexes with widely differing geometries perhaps because this is a reactive site. In 8M urea many of the same cleavage sites appear along with several new sites. Thus some structure appears to be retained, but this is consistent with other studies suggesting that the secondary structure of t-RNA is quite robust.

RNA in RNA-DNA hybrids is not cleaved at 37° C. by $Eu(L^1)^{3+}$ under conditions where all other nucleotides are cleaved. Although it cannot be ruled out the fact that the loss of nuclease activity may be a result of poorer binding of the metal ion to the hybrid than to a flexible single stranded RNA it is likely that the more rigid conformation of RNA in duplex form plays a large role. Phosphate esters of RNA in a helical form are in the wrong conformation to undergo nucleophilic attack and displacement of the 5'-hydroxyl in an in-line displacement mechanism. Studies have shown that RNA cleavage in the presence of ethylene diamine proceeds five times more rapidly for single-stranded RNA than for RNA in a triple helix. If reactivity changes upon duplex formation, then it may be advantageous in the construction of antisense oligonucleotides to place the RNA transesterification catalyst on the end of the oligonucleotide in close proximity to a more flexible section of RNA.

EXAMPLE VI

Conjugation of macrocycles to oligonucleotides

1. Synthesis of Macrocycle

Synthesis of 4-[(1,4,8,11-tetraazacyclotetradec-1-yl)methyl]benzoic acid (1 in FIG. 5) was according to a modified method of Studer et al., *Helo. Chim. Acta*, 1986, vol. 69, p. 2081, which disclosure is hereby incorporated by reference. Cyclam (2 g, 10 mmol) was dissolved in a mixture of ethanol (30 m) and water (6 m). To this solution was added a solution of 4-bromobenzoic acid (0.428 g, 2 mmol) in aqueous LiOH (0.100 g in 8 mL of water). The acid was dissolved by gentle heating. The resultant mixture was refluxed vigorously with stirring for 5 hours. The solvent was removed in vacuo and the residue dissolved in a minimum amount of water. The solution obtained was extracted with chloroform (5 mL×10) and the aqueous layer was concentrated down to 2 mL. A solution of concentrated HCl (2 mL) and ethanol (2 mL) was then added. A white solid precipitated upon standing for four hours. The solid was recrystallized from ethanol/water/HCl. Yield was 0.400 g of tetrahydrochloride salt having a Mp 272–276, and satisfactory $^1H$ NMR. FABMS m/z 335 (M+1)

Macrocycle (1, FIG. 5) was dried over $P_2O_5$ at 50° C. for 5 hours immediately before use. All manipulations were carried out under argon. To a round bottom flask was added successively the macrocycle (1, FIG. 5) (0.150 g, 0.32 mmol), dry methanol (1.5 mL) and dry triethyl amine (0.75 mL) and trifluoroethylacetate (2.5 mL). The mixture was stirred for 48 hours. Solvents were removed in vacuo and the residue was taken up in dry tetrahydrofuran. The tetrahydrofuran solution was filtered, the solvent removed in vacuo, and the residue dried in vacuo for 6 hours. The flask was purged with argon three times. Dry tetrahydrofuran (1.5 mL) was added followed by N-hydroxysuccinimide (0.040 g, 0.40 mmol) and 1-ethyl-3-[3-(dimethylamino)propyl] carbodiimide (EDC) (0.075 g, 0.37 mmol). The mixture was stirred under argon for 48 hours and the solvent removed in vacuo. The residue was dissolved in a minimum amount of chloroform and loaded on a silica gel column (1.5×50 cm) packed in chloroform. The column was washed with chloroform (2×2 mL). The product was eluted with chloroform: methanol mixture (100:1). Fractions containing macrocycle 4-[(1,4,8,11-tris(trifluoroacetyl)-1,4,8,11-tetraazacyclodec-1-yl)methyl]benzoic acid, N-hydroxysuccinimide ester (2 in FIG. 5), were combined and concentrated. The concentrated solution (2) was taken to dryness under vacuo at 45°–50° C. to yield 140 mg a fluffy white solid. $^1H$ NMR data was as expected. FABMS (M+1) 720.

2. Conjugation of cyclam derivative to oligonucleotide

A solution of (2) (1.2 mg) in dioxane (0.080 mL) was added to a solution of a 16-mer oligonucleotide containing a 5'-$C_{12}$ methylene amino linker (Oligos inc.) (1 AU) in $NaHCO_3$ (0.150 mL, 200 mM, pH 9.0) and the resultant mixture was stirred vigorously for 3 hours. The reactant mixture was loaded onto a sephadex G-25 (1×8 cm) column packed in potassium phosphate buffer (100 mM, pH 7.0). The product was eluted with the same phosphate buffer. Three 3 mL fractions were collected. The last two fractions were mixed and reduced in volume to 0.5 mL. The solution was filtered through a 0.22 micron nylon filter into a microfuge tube. The closed tube was heated at 55° C. for twenty hours to remove the trifluoroacetate protecting groups from the macrocycle. To ensure that complete deprotection had occurred, HPLC analysis of the product was carried out on a C-18 reverse phase column (5 µm, 4.6×150 mm) using a mixture of triethylammonium acetate buffer A (100 mM, pH 7.0) and acetonitrile (B) at a flow rate of 1 mL/min. (96% A for 2 min, 4%–40% B, linear gradient, over 25 min, 40% B for 5 min. The product eluted as a single peak between 21.5 and 23 min. The product was collected and the solvent was removed in a speed vac at 55° C. for 15 h. Yield was about 0.5–0.6 unit.

EXAMPLE VII

Figure 6:
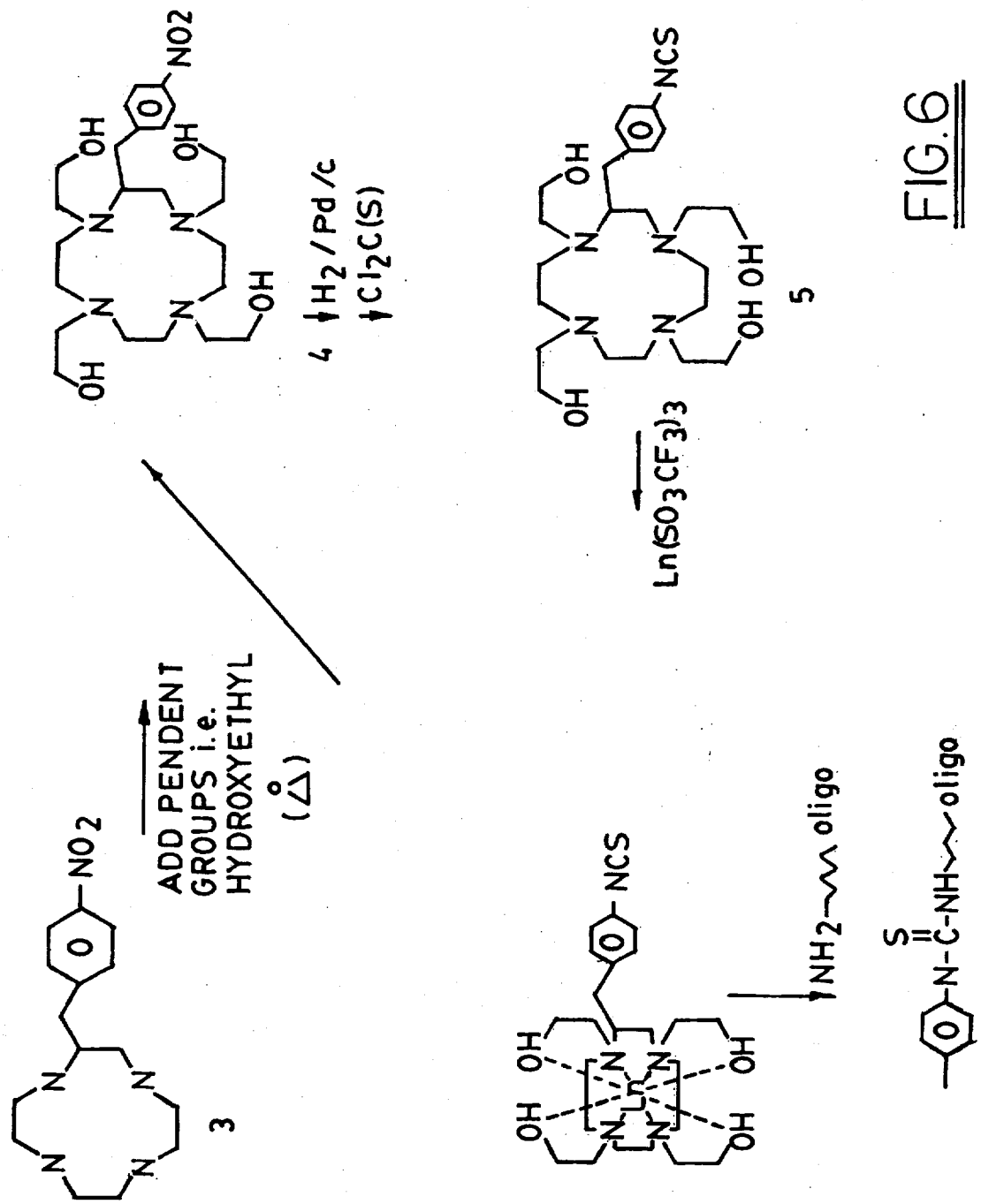
FIG. 6 shows the synthesis of 1,4,7,10-tetrakis(2-hydroxyethyl)-1,4,7,10-tetraazacyclododecane and conjugation to an oligonucleotide.

Conjugation of 1,4,7,10-tetrakis(2-hydroxyethyl)-1,4,7,10-tetraazacyclododecane to an oligonucleotide Synthesis of a cyclen containing a functional group for attachment to biomacromolecules is conducted according to the method of Rennet al., *Bioconjugate Chem.*, 1992, vol. 3, pp. 563–569, which disclosure is hereby incorporated by reference, to obtain the macrocycle 3 (FIG. 6). Addition of pendent groups (i.e., hydroxyethyl) will follow to give the complex 4 (FIG. 6). Then, the nitro group is converted to an isothiocyanate. The macrocycle 5 (FIG. 6) is then treated with $Eu(SO_3CF_3)_3$ in acetonitrile as previously described. The lanthanide macrocycle 6 (FIG. 6) is conjugated to an oligonucleotide containing a primary amine. Alternatively, the macrocycle may be conjugated to the oligonucleotide followed by treatment of the oligonucleotide-macrocycle conjugate with $Eu(SO_3CF_3)_3$.

EXAMPLE VIII

Conjugation And Linkers

Linking small molecules to oligonucleotides is described by Eckstein, "Oligonucleotides and Analogs: A Practical Approach," Oxford press, N.Y., 1991, which reference is hereby incorporated by disclosure. Modification of oligonucleotides with different linkers is described by Goodchild, *Bioconjugate Chem.*, 1990, vol. 1, pp. 165–186, which disclosure is hereby incorporated by reference. For example, linkers may be attached to either the 5' phosphate or the 3' phosphate of the oligonucleotide, an internal phosphate or to a base. Any known linker group can be employed herein provided the oligonucleotide provide sequence specific RNA cleavage and/or suppresses of M-RNA translation. Different types of modified oligonucleotides might also be used such as methyl phosphonates or amine oxides, or phosphorothioates.

The present invention provides metal complexes which promote catalytic cleavage of RNA by transesterification.

Although the present invention has been described in detail by way of illustration and Examples, it will be obvious that changes and modifications may be practiced within the scope of the appended claims.

We claim:

1. A macrocyclic complex having the formula:

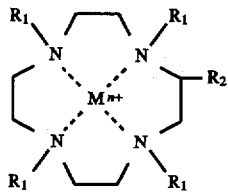

wherein $R_1$ is selected from the group consisting of $CH_2CH_2OH$, $CH_2CH(CH_3)OH$, and $CH_2C(O)NH_2$, provided that when $R_1$ is $CH_2CH_2OH$, $M^{n+}$ is $Eu^{3+}$ or $Gd^{3+}$, provided that when $R_1$ is $CH_2CH(CH_3)OH$, $M^{n+}$ is $La^{3+}$ or $Eu^{3+}$, and provided that when $R_1$ is $CH_2C(O)NH_2$, $Mn^+$ is $La^{3+}$; and wherein $R_2$ is selected from the group consisting of hydrogen, alkyl, or aryl.

2. A macrocyclic complex according to claim 1, wherein $R_1$ is $CH_2CH_2OH$ and $M^{n+}$ is $Eu^{3+}$.

3. A macrocyclic complex according to claim 1, wherein $R_1$ is $CH_2CH_2OH$ and $M^{n+}$ is $Gd^{3+}$.

4. A macrocyclic complex according to claim 1, wherein $R_1$ is $CH_2CH(CH_3)OH$, and $M^{n+}$ is $La^{3+}$.

5. A macrocyclic complex according to claim 1, wherein $R_1$ is $CH_2CH(CH_3)OH$ and $M^{n+}$ is $Eu^{3+}$.

6. A macrocyclic complex according to claim 1, wherein $R_1$ is $CH_2C(O)NH_2$ and $M^{n+}$ is $La^{3+}$.

7. A method of forming a macrocyclic complex, comprising reacting a metal ion selected from the group consisting of $Eu^{3+}$, $Gd^{3+}$, and $La^{3+}$, with a non-metallic ion or molecule having the formula:

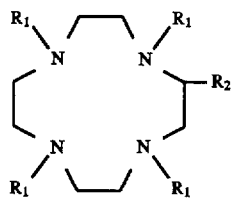

wherein $R_1$ is selected from the group consisting of $CH_2CH_2OH$, $CH_2CH(CH_3)OH$, and $CH_2C(O)NH_2$, provided that when $R_1$ is $CH_2CH_2OH$, the metal ion is $Eu^{3+}$ or $Gd^{3+}$, provided that when $R_1$ is $CH_2CH(CH_3)OH$, the metal ion is $La^{3+}$ or $Eu^{3+}$, and provided that when $R_1$ is $CH_2C(O)NH_2$, the metal ion is $La^{3+}$ and wherein $R_2$ is selected from the group consisting of hydrogen, alkyl, or aryl under conditions which facilitate attachment of the metal ion to the non-metallic ion or molecule, thereby forming the macrocyclic complex.

8. A method according to claim 7, wherein $R_1$ is $CH_2CH_2OH$ and the metal ion is $Eu^{3+}$.

9. A method according to claim 7, wherein $R_1$ is $CH_2CH_2OH$ and the metal ion is $Gd^{3+}$.

10. A method according to 7, wherein $R_1$ is $CH_2CH(CH_3)OH$ and the metal ion is $La^{3+}$.

11. A method according to 7, wherein $R_1$ is $CH_2CH(CH_3)OH$ and the metal ion is $Eu^{3+}$.

12. A method according to claim 7, wherein $R_1$ is $CH_2C(O)NH_2$ and the metal ion is $La^{3+}$.

13. A method according to claim 7, wherein said reacting is carried out under anhydrous conditions.

14. A method according to claim 13, wherein said reacting is carried out in the presence of trimethyl orthoformate.

* * * * *

UNITED STATES PATENT AND TRADEMARK OFFICE
CERTIFICATE OF CORRECTION

PATENT NO. : 5,684,149
DATED : November 4, 1997
INVENTOR(S) : Janet R. Morrow

Page 1 of 1

Figure 5:
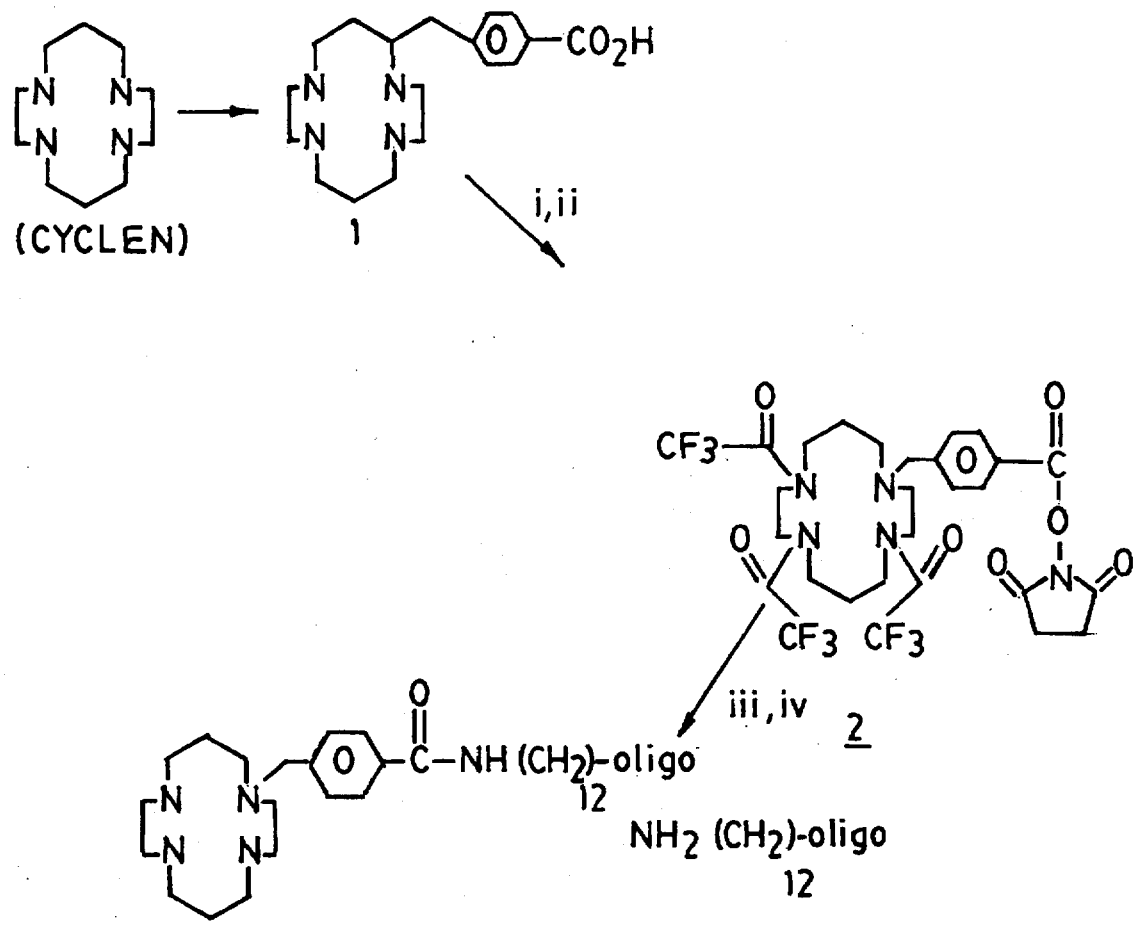
FIG. 5 shows the synthesis of the cyclam derivative 4-[(1,4,8,11-tetraazacyclotetradec-1-yl)methyl] benzoic acid and conjugation to an oligonucleotide.

It is certified that error appears in the above-identified patent and that said Letters Patent is hereby corrected as shown below:

Cancel Figure 5 and insert therefore Figure 5 (Amended), which is attached hereto.

Column 5,
Line 55, delete the chemical group "$CH_2\text{-}O(Me)(O)_2\text{-}$" and insert therefore the chemical group -- $CH_2CH(CH_3)OH$ --.

Signed and Sealed this

Twenty-first Day of August, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO. : 5,684,149
DATED : November 4, 1997
INVENTOR(S) : Janet R. Morrow

Page 1 of 1

It is certified that error appears in the above-identified patent and that said Letters Patent is hereby corrected as shown below:

Cancel Figure 5, and insert therefore Figure 5 (Amended), which is attached hereto.

Column 5,
Line 55, delete the chemical group "$CH_2-O(Me)(O)_2-$" and insert therefore the chemical group -- $CH_2CH(CH_3)OH$ --.

Signed and Sealed this

First Day of January, 2002

Attest:

*Attesting Officer*

JAMES E. ROGAN
*Director of the United States Patent and Trademark Office*